United States Patent [19]

Savage et al.

[11] Patent Number: 5,561,275
[45] Date of Patent: Oct. 1, 1996

[54] HEADSET FOR ELECTRONIC STETHOSCOPE

[75] Inventors: Gary Savage, Montréal; Michel Swift, Outremont, both of Canada

[73] Assignee: Delstar Services Informatiques (1993) Inc., Montreal, Canada

[21] Appl. No.: 234,254

[22] Filed: Apr. 28, 1994

[51] Int. Cl.$^6$ ............................................. A61B 7/02
[52] U.S. Cl. ........................................... 181/131; 381/67
[58] Field of Search ............................... 181/129, 131, 181/135, 137; 381/67; 2/209; 128/715

[56] References Cited

U.S. PATENT DOCUMENTS

| | | |
|---|---|---|
| D. 246,782 | 12/1977 | Saiya . |
| D. 335,709 | 5/1993 | Choi . |
| 3,346,069 | 10/1967 | Speelman ................................ 181/135 |
| 3,539,032 | 10/1970 | Scanlon .................................. 181/135 |
| 3,667,569 | 6/1972 | Mackey et al. . |
| 3,681,540 | 8/1972 | Thomson . |
| 3,710,888 | 1/1973 | Peart . |
| 3,746,124 | 7/1973 | Wilson et al. . |
| 3,789,164 | 1/1974 | Ryder . |
| 3,829,624 | 8/1974 | Goodin et al. . |
| 3,993,161 | 11/1976 | Shore . |
| 4,055,233 | 10/1977 | Huntress . |
| 4,149,610 | 4/1979 | Saiya et al. . |
| 4,200,169 | 4/1980 | MacDonald et al. . |
| 4,261,432 | 4/1981 | Gunterman . |
| 4,282,678 | 8/1981 | Tsui . |
| 4,406,346 | 9/1983 | Pope . |
| 4,618,986 | 10/1986 | Hower . |
| 4,727,585 | 2/1988 | Flygstad . |
| 4,783,822 | 11/1988 | Toole et al. . |
| 4,852,684 | 8/1989 | Packard . |
| 4,864,610 | 9/1989 | Stevens . |
| 4,878,560 | 11/1989 | Scott . |
| 4,913,259 | 4/1990 | Packard . |
| 5,111,904 | 5/1992 | Packard et al. . |
| 5,189,264 | 2/1993 | Peart . |
| 5,288,953 | 2/1994 | Peart . |
| 5,288,954 | 2/1994 | Peart et al. . |

FOREIGN PATENT DOCUMENTS

| | | |
|---|---|---|
| 2227673 | 1/1974 | Germany . |
| 3909011A1 | 10/1989 | Germany . |
| 26679 | of 1912 | United Kingdom . |

*Primary Examiner*—Khanh Dang
*Attorney, Agent, or Firm*—Merchant, Gould, Smith, Edell, Welter, Schmidt, P.A.

[57] ABSTRACT

The headset comprises left and right elongate ear pieces having respective first ends to receive ear tips and respective, interconnected second ends. Each ear piece includes a one-piece elongate body made of flexible and resilient material and curved outwardly to skirt round the user's head when the ear tips are applied to a user's ears. The elongate body is formed with a first length of smaller cross section and therefore of greater flexibility proximate the second end of the corresponding ear piece and with a second length of lower flexibility situated between that first length and the corresponding ear tip. Bending of the elongate bodies when the ear pieces are spread apart is therefore concentrated in the first lengths and pressure applied to the user's ears by the ear tips is mainly produced by the bent first lengths and transmitted to the ear tips through the second lengths of lower flexibility. The elongate ear pieces have respective second end sections assembled laterally adjacent to each other, and a threaded sleeve is mounted on these laterally adjacent second end sections and is rotated and displaced longitudinally to adjust the level of pressure applied to the user's ears by the ear tips.

9 Claims, 3 Drawing Sheets

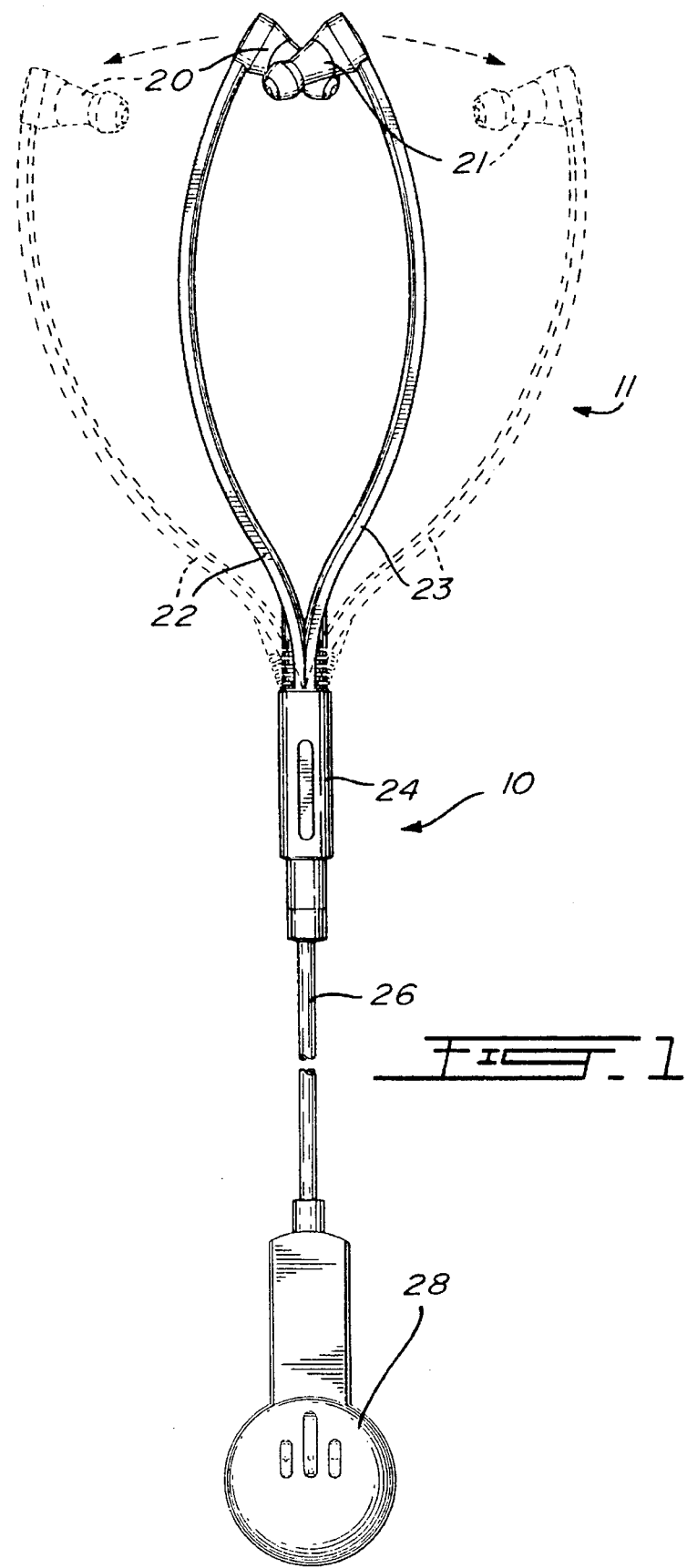

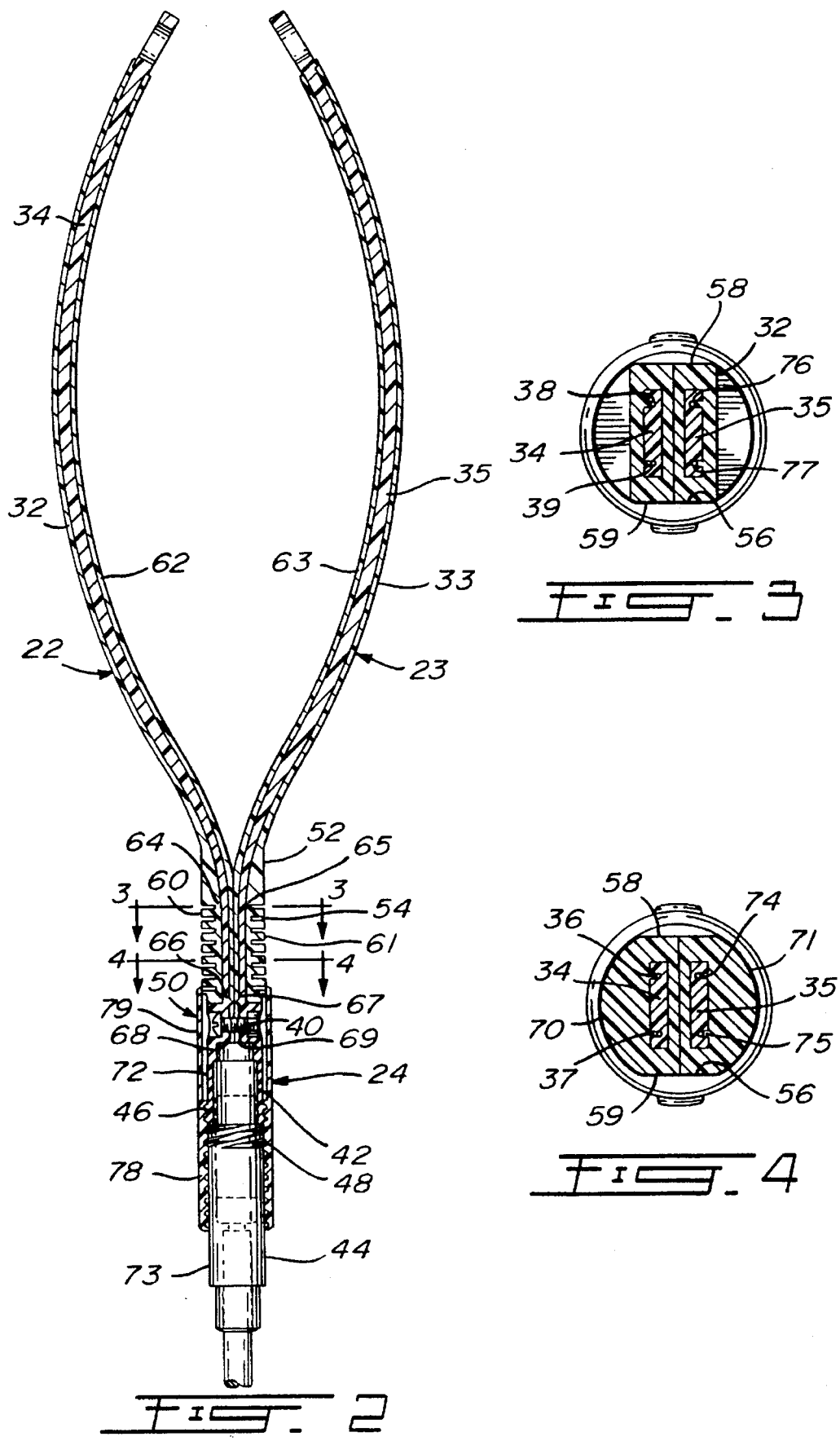

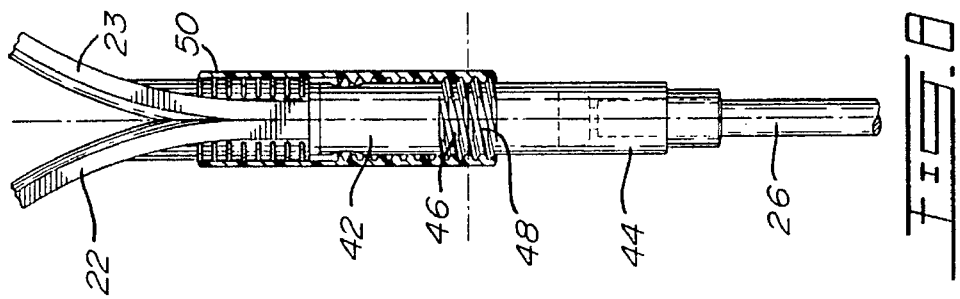
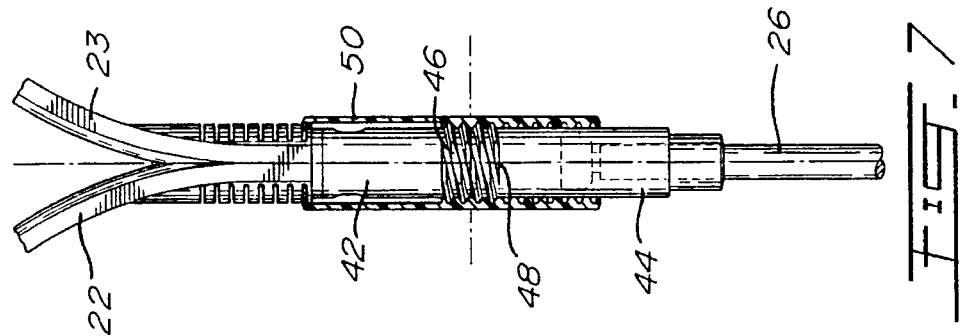
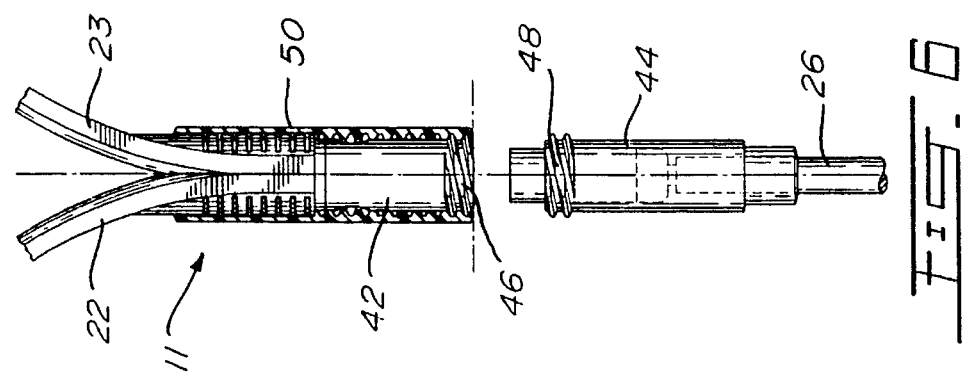
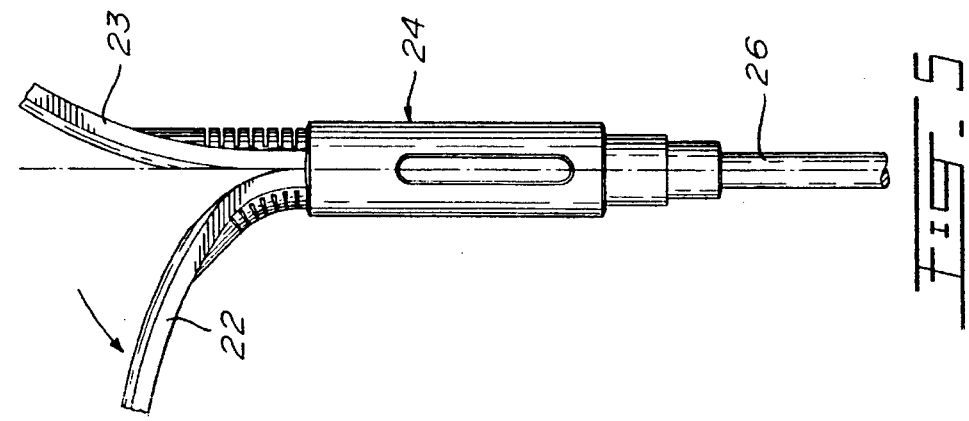

HEADSET FOR ELECTRONIC STETHOSCOPE

BACKGROUND OF THE INVENTION

1. Field of the Invention

The present invention relates generally to a headset, more specifically to a headset for electronic stethoscope providing for adjustment of the pressure applied to the ears of the user by the ear tips.

2. Brief Description of the Prior Art

Many prior art methods have been used to apply with sufficient pressure the ear tips of a stethoscope to the ears of the user. One method consists of interconnecting the lower ends of the two elongate ear pieces through a spring element which is deformed and tensioned when the ear pieces are spread apart to apply the ear tips to the user's ears. The ear pieces tend to return to their original position to thereby hold the ear tips on the user's ears.

A drawback of this prior art method is that the level of pressure applied to the ears by the ear tips is not adjustable whereby insufficient or excessive pressure may be produced. For example, excessive pressure is detrimental to the user's comfort and can even lead to tissue damage under prolonged use.

Other prior art methods have been proposed to adjust the pressure applied to the user's ears by the ear tips. However, these methods are generally complex, costly and/or difficult to implement and use. An example is described in U.S. Pat. No. 3,746,124 granted to Wilson, deceased et al. on Jul. 17, 1973.

OBJECTS OF THE INVENTION

A general object of the present invention is to overcome the above discussed drawbacks of the prior art.

Another object of the invention is to provide a headset in which the pressure applied to the ears by the ear tips is easily adjustable, even when the headset is worn.

SUMMARY OF THE INVENTION

More specifically, in accordance with the present invention, there is provided an ear piece for headset comprising a one-piece elongate body made of flexible and resilient material. This elongate body comprises a first end for receiving an ear tip to be applied to a user's ear and a second end to be connected to the rest of the headset; it is also curved to skirt round the user's head when the ear tip is applied to the user's ear. This elongate body is formed with a length of smaller cross section and therefore of greater flexibility proximate the second end thereof whereby bending of the elongate body for applying the ear tip to the user's ear is concentrated in the length of smaller cross section and greater flexibility.

Adjustment of the pressure applied by the ear tip to the user's ear is therefore carried out at the level of the length of smaller cross section and of greater flexibility.

Also in accordance with the present invention, there is provided a headset for applying ear tips to a user's ears, comprising left and right elongate ear pieces each having a first end structured to receive one of the ear-tips and having respective, interconnected second ends. Each ear piece comprises a one-piece elongate body made of flexible and resilient material and curved outwardly to skirt round the user's head when the ear tips are applied to the user's ears. Each elongate body is formed with a first length of smaller cross section and therefore of greater flexibility proximate the second end of the corresponding ear piece and with a second length of lower flexibility situated between the first length and the first end of the corresponding ear piece.

In operation, bending of the elongate bodies when the ear pieces are spread apart to apply the ear tips to the user's ears is concentrated in the first lengths and accordingly pressure applied to the user's ears by the ear tips is mainly produced by the bent first lengths and transmitted from these first lengths to the ear tips through the second lengths of lower flexibility.

In accordance with a preferred embodiment of the invention, each first length of smaller cross section and of greater flexibility gradually passes from a first cross section of larger area to a second cross section of smaller area as the distance from the second end of the corresponding ear piece reduces.

According to another preferred embodiment of the present invention, the one-piece elongate body of each ear piece comprises at least one longitudinal groove to form a channel in which at least one electric wire extends from the corresponding ear tip to the second end of the corresponding ear piece. An envelope of plastic material is molded over each elongate body and therefore covers the longitudinal groove and wire.

Advantageously, each elongate body being made of flexible and resilient plastic material, the plastic material of the envelope molded over each elongate body has mechanical properties selected to reduce flexibility of the corresponding elongate body.

Further in accordance with the present invention, there is provided a headset for applying ear tips to a user's ears, comprising left and right elongate ear pieces each having a first end structured to receive one of the ear tips and having respective second end sections. Each ear piece is curved outwardly to skirt round the user's head when the ear tips are applied to the user's ears, and is flexible and resilient over a given length thereof. The headset further comprises means for assembling the second end sections of the ear pieces laterally adjacent to each other, and means for displacing the assembling means longitudinally on the laterally adjacent second end sections to thereby adjust the level of pressure applied to the user's ears by the ear tips when the ear pieces are spread apart to apply the ear tips to the user's ears.

Preferably, the assembling means comprises a sleeve internally threaded over at least a portion of its length and mounted on the laterally adjacent second end sections, and the headset comprises a generally cylindrical outer threaded surface axial with the laterally adjacent second end sections and on which the sleeve is screwed whereby rotation of the sleeve causes longitudinal displacement of that sleeve on the laterally adjacent second end sections to thereby adjust the level of pressure applied to the user's ears by the ear tips.

The objects, advantages and other features of the present invention will become more apparent upon reading of the following non restrictive description of a preferred embodiment thereof, given by way of example only with reference to the accompanying drawings.

BRIEF DESCRIPTION OF THE DRAWINGS

In the appended drawings:

FIG. 1 is a front elevational view of an electronic stethoscope comprising a headset in accordance with the present invention;

FIG. 2 is an enlarged, partly cross sectional view of a pressure adjusting mechanism of the stethoscope's headset of FIG. 1, comprising a sleeve mounted on the laterally adjacent lower end sections of the two elongate ear pieces of this headset;

FIG. 3 is a cross sectional view of the headset taken along line 3—3 of FIG. 2;

FIG. 4 is a cross sectional view of the headset taken along line 4–4 of FIG. 2;

FIG. 5 is a front elevational view of the pressure adjusting mechanism of FIG. 2, showing the maximum angle of deflection of an ear piece;

FIG. 6 is a front, partly cross sectional elevational view of the pressure adjusting mechanism showing how a connector forming part of a cable of the stethoscope's thoracic coupler is assembled;

FIG. 7 is a front, partly cross sectional elevational view of the pressure adjusting mechanism in a position in which the pressure applied to a user's ears by the ear tips is minimum; and FIG. 8 is a front, partly cross sectional elevational view of the pressure adjusting mechanism in a position in which the pressure applied to the ears of the same user is maximum.

DETAILED DESCRIPTION OF THE PREFERRED EMBODIMENT

Referring to FIG. 1 of the appended drawings, a stethoscope 10 is illustrated. The stethoscope 10 comprises a headset 11, a thoracic coupler 28, and an electric cable 26 interconnecting the thoracic coupler 28 and the headset 11. The headset 11 essentially comprises left and right ear tips 20 and 21, left and right elongate ear pieces 22 and 23, and a pressure adjusting mechanism 24.

In the preferred embodiment of the invention, the stethoscope 10 is an electronic stethoscope. Accordingly, the thoracic coupler 28 comprises an electroacoustic transducer (not shown) for converting sounds produced by the patient's body into an electric signal, and an electronic circuit (not shown) for amplifying and filtering this electric signal before it is supplied to miniature loudspeakers (not shown) encased in the ear tips 20 and 21. Therefore, the miniature loudspeakers reproduce the sounds picked up by the thoracic coupler 28 to allow the user of the stethoscope to listen thereto.

FIG. 1 also illustrates in dashed lines spreading apart of the two ear pieces 22 and 23 for applying the ear tips 20 and 21 to the user's ears. As can be seen, each ear piece 22,23 is curved outwardly to skirt round the user's head when the ear tips 20 and 21 are applied to the user's ears.

Referring to FIGS. 1 and 2, the left and right ear pieces 22 and 23 each have an upper end structured to receive the corresponding one of the ear tip 20 or 21. The ear pieces 22 and 23 further comprise lower end sections 60 and 61 assembled laterally adjacent to each other.

The ear pieces 22 and 23 are identical and each comprise a one-piece elongate inner body 34,35 made of flexible and resilient material enveloped by soft plastic material 32,33 molded over the elongate body 34,35. The elongate body 34,35 can be made for example of plastic material such as Delrin® and the soft plastic material 32,33 may comprise flexible PVC (polyvinyl chloride), rubber material, etc.

The elongate body 34,35 have a constant width (FIGS. 3 and 4) but gradually passes from a first larger thickness (point 62,63) to a smaller thickness (point 64,65) as the distance from lower end 68,69 of the elongate body 34,35 reduces. Between point 64,65 and point 66,67, the elongate body 34,35 has a constant thickness equal to that at point 64,65. The elongate body 34,35 is accordingly formed with a first length of smaller cross section and therefore of greater flexibility between point 62,63 and point 66,67 and with a second length of constant cross section and of lower flexibility situated between point 62,63 and the upper end of the elongate body 34,35. Thus, bending of the elongate bodies 34 and 35 when the ear pieces 22 and 23 are spread apart (FIG. 1) to apply the ear tips 20 and 21 to the user's ears is concentrated in the first lengths and pressure applied to the user's ears by the ear tips 20 and 21 is mainly produced by the bent first lengths and transmitted from these first lengths to the ear tips 20 and 21 through the second lengths of lower flexibility.

The envelope 32,33, made of soft plastic material, has a thickness that increases from point 62,63 toward the lower end 68,69 of the elongate body 34,35. More specifically, the thickness of the envelope 32,33 varies in function of the cross section of the inner elongate body 34,35 to keep the cross section of the ear piece 22,23 essentially constant from the ear tips 20 and 21 to the lower end section 60,61. Also, the soft plastic envelope 32,33 of the lower end section 60,61 defines a semicylindrical outer surface 70,71 (FIG. 4). Accordingly, the soft plastic envelopes 32 and 33 of the laterally adjacent lower end sections 60 and 61 defines a cylindrical outer surface 52 of essentially constant diameter. The cylindrical surface 52 is formed with lateral, transversal grooves such as 54 to prevent interference of the envelopes 32 and 33 to bending of the elongate bodies 34 and 35 and therefore to bending of the elongate ear pieces 22 and 23 (see FIG. 1).

The main function of the envelopes 32 and 33 is to cover the elongate bodies 34 and 35 with soft material in order to improve the comfort of the headset's user. However, it is important to point out that the flexibility of the soft plastic material of the envelopes 32 and 33 can be reduced in view of increasing the rigidity, thus reducing the flexibility of the elongate ear pieces 22 and 23. Indeed, as the elongate bodies 34 and 35, and the respective envelopes 32 and 33 can be considered as being laminated, the mechanical properties of their materials can be selected to cooperate together to give a desired degree of rigidity and flexibility to the ear pieces 22 and 23.

As illustrated in FIG. 2, the lower ends 68 and 69 of the elongate bodies 34 and 35 are interconnected through a bolt-and-nut fastener 40. The lower ends 68 and 69 of the elongate bodies 34 and 35 advantageously prolong downwardly to form respective semicylindrical extensions assembled together to form a cylindrical receptacle 42 incorporating or capable of receiving an electric female connector. The receptacle 42 defines an outer cylindrical surface 72 of which the lower portion 46 is threaded.

The cable 26 (FIG. 1) interconnecting the thoracic coupler 28 and the headset 11 is provided at the end thereof opposite to the coupler 28 with another electric male connector 44 (FIG. 2) fitting in the receptacle 42 to electrically connect the thoracic coupler 28 with the headset 11 through the cable 26. Electric connector 44 comprises a cylindrical outer surface 73 having an upper threaded portion 48. When connector 44 is inserted in receptacle 42 (FIG. 2), the threaded portions 46 and 48 are longitudinally adjacent to each other to form a single continuous thread.

To interconnect the receptacle 42 with the miniature loudspeakers (not shown) mounted in the ear tips 20 and 21, the elongate body 34 comprise a pair of longitudinal grooves 36 and 37 (FIGS. 3 and 4) to receive respective wires 38 and 39. In the same manner, the elongate body 35 comprise a pair of longitudinal grooves 74 and 75 (FIGS. 3 and 4) to receive respective wires 76 and 77. The grooves 36, 37, 74 and 75 form longitudinal channels in which the respective electric wires 38, 39, 76 and 77 extend from the ear tips 20 and 21 to the receptacle 42. As can be appreciated, the soft plastic envelope 32 covers both the grooves 36 and 37 and the wires 38 and 39, while envelope 33 covers both the grooves 74 and 75 and the wires 76 and 77.

Therefore, the electric signals representative of the sounds picked up by the thoracic coupler 28 (FIG. 1) are transmitted from that thoracic coupler 28 to the miniature loudspeakers (not shown) of the ear tips 20 and 21 through the cable 26, connector 44, receptacle 42, and wires 38, 39, 76 and 77.

The pressure adjusting mechanism 24 (FIGS. 1 and 2) comprises the threaded portion 46 and a hollow sleeve 50 having a lower half portion 78 internally threaded. Assembly of the sleeve 50 to the headset 11 is illustrated in FIG. 6. The internally threaded portion 78 of the sleeve 50 is first screwed onto the threaded portion 46 of receptacle 42 until the sleeve 50 reaches the position of FIG. 6. Male connector 44 is then inserted in the receptacle 42 and the sleeve 50 is screwed onto threaded portion 48. Of course, in the position of FIG. 6, the male connector 44 can be inserted in and removed from the receptacle 42 at will. The threaded lower portion 78 of the sleeve 50 is then engaged on both the longitudinally adjacent threaded portions 46 and 48 as illustrated in FIG. 2. Accordingly, a function of the sleeve 50 is to hold the male connector 44 in the receptacle 42.

Further rotation of the sleeve 50 on the threaded portions 46 and 48 will displace the sleeve 50 longitudinally along the laterally adjacent end sections 60 and 61 of the ear pieces 22 and 23. To enable longitudinal displacement of the sleeve 50, the inner diameter of the upper unthreaded portion 79 of the sleeve 50 is slightly larger than the outer diameter of the cylindrical surface 52. The sleeve 50 is rotated clockwise or counterclockwise depending on the desired axial direction of displacement.

FIGS. 5 and 7 show the sleeve 50 in a lowest position. In this position, the lengths of smaller diameter of the elongate bodies 34 and 35 are situated outside the sleeve 50 to facilitate deflection of the ear pieces 22 and 23 and to produce a weakest pressure on the ear tips 20 and 21.

In FIG. 8, the sleeve is in the highest position. In this position, an important part of the lengths of smaller diameter and therefore of greater flexibility of the elongate bodies 34 and 35 are situated inside the sleeve 50 to render deflection of the ear pieces 22 and 23 more difficult and to produce a strongest pressure on the ear pieces 22 and 23 when they are spread apart to apply the ear tips 20 and 21 on the user's ears.

Referring to FIGS. 3 and 4, the sleeve 50 is formed with a longitudinal flat surface portion 56 projecting from the inner generally cylindrical surface of the upper unthreaded sleeve portion 79, while the outer cylindrical surface 52 of the laterally adjacent end sections 60 and 61 comprises front and rear diametrically opposed flat surface portions 58 and 59. At each revolution of the sleeve 50, the inner flat surface portion 56 of the sleeve 50 will deform the envelopes 32 and 33 of soft plastic material to cause resistance to rotation of the sleeve 50 and to releasably block the sleeve 50 in position on the laterally adjacent second end sections 60 and 61 when the inner flat surface portion 56 is applied to one of the outer flat surface portion 58 or 59. This will prevent undesirable rotation of the sleeve 50 leading to a change in the adjustment of the pressure applied to the user's ears by the ear tips 20 and 21.

Undesirable rotation of the sleeve 50 can also be prevented through friction by appropriately dimensioning the inner diameter of the sleeve 50 and to outer diameter of the cylindrical surface 52, and/or by appropriately dimensioning the respective diameters of the threaded portions 46, 48 and 78.

Although the present invention has been described hereinabove by way of a preferred embodiment thereof, this embodiment can be modified at will, within the scope of the appended claims, without departing from the spirit and nature of the subject invention.

What is claimed is:

1. An ear piece for headset for applying an ear tip to a user's ears comprising a bendable elongate body made of flexible and resilient plastic material, said elongate body being curved to skirt round the user's head when the ear tip is applied to the user's ear, and said elongate body comprising:

proximate end to be connected to the headset;

a distal end structured to receive the ear tip;

a weakened first portion proximate said proximate end; and a second portion situated between said distal end and the weakened first portions;

wherein the weakened first portion has a first flexibility and the second portion has a second flexibility lower than said first flexibility whereby bending of the elongate body for applying the ear tip to the user's ear is concentrated in said weakened first portion.

2. An ear piece for headset as defined in claim 1, further comprising at least one electric wire, wherein said elongate body comprises at least one longitudinal channel in which said at least one electric wire extends from said proximate end to said distal end of the elongate body.

3. An ear piece for headset as defined in claim 1, wherein the weakened first portion comprises transversal outer grooves to facilitate bending of the weakened first portion.

4. A headset for applying ear tips to a user's ear, comprising left and right elongate ear pieces each having a distal end structured to receive one of the ear tips and having respective, interconnected proximate ends, each of said ear pieces comprising a bendable elongate body made of flexible and resilient plastic material and curved outwardly to skirt round the user's head when the ear tips are applied to the user's ears, wherein each elongate body formed with a first length of smaller cross section and therefore comprises:

a weakened first portion proximate said proximate end of the corresponding ear piece; and a second portion situated between said first portion and said distal end of the corresponding ear piece;

wherein said first portion has a first flexibility and said second portion has a second flexibility lower than said first flexibility whereby bending of the elongate bodies when the ear pieces are spread apart to apply the ear tips to the user's ears is concentrated in said weakened first portions and whereby pressure applied to the user's ears by the ear tips is mainly produced by the bent first portions and transmitted from said first portions to the ear tips through said second portions.

5. A headset as recited in claim 4, wherein each ear piece comprises at least one electric wire, and wherein the elongate body of each ear piece comprises at east one longitudinal channel in which said at least one electric wire of said ear piece extends from the distal end to the proximate end of said ear piece.

6. A headset as recited in claim 4, further comprising a sleeve member in which the weakened first portions of the elongate bodies of the left and right ear pieces are mounted laterally adjacent to each other, the sleeve member comprising means for displacing said sleeve member longitudinally on the laterally adjacent weakened first portions to thereby adjust the level of pressure applied to the user's ears by the ear tips when the ear pieces are spread apart to apply the ear tips to the user's ears.

7. The headset of claim 6, wherein said sleeve member comprises a sleeve internally threaded over at least a portion of its length, and wherein said headset comprises a generally cylindrical externally threaded sleeve-receiving member axial with said laterally adjacent weakened first portions and on which the sleeve is screwed whereby rotation of said sleeve causes longitudinal displacement of said sleeve on the laterally adjacent weakened first portions to thereby adjust the level of pressure applied to the user's ears by the ear tips.

8. The headset of claim 6, wherein each ear piece comprises at least one electric wire, and wherein the elongate body of each ear piece comprises at least one longitudinal channel in which said at least one electric wire of said ear piece extends from the distal end to the proximate end of said ear piece.

9. A headset as recited in claim 4, wherein the weakened first portion of each elongate body comprises transversal outer grooves to facilitate bending of said weakened first portion.

* * * * *

UNITED STATES PATENT AND TRADEMARK OFFICE
CERTIFICATE OF CORRECTION

PATENT NO. : 5,561,275

DATED : October 1, 1996

INVENTOR(S) : Gary Savage, Michel Swift

It is certified that error appears in the above-identified patent and that said Letters Patent is hereby corrected as shown below:

On title page, item [75] Inventors:, please delete "Gary" and insert --Garry-- therefor.

Signed and Sealed this

Fourth Day of November, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,561,275

DATED : October 1, 1996

INVENTOR(S) : Gary Savage, Michel Swift

It is certified that error appears in the above-identified patent and that said Letters Patent is hereby corrected as shown below:

On the cover page, item [75] Inventors:, please delete "Gary" and insert --Garry-- therefor.

On the cover page, item [73] Assignee:, please delete "Delstar Services Informatiques (1993) Inc." and insert --Theratechnologies Inc.-- therefor.

Signed and Sealed this

Third Day of March, 1998

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,561,275

DATED : OCTOBER 1, 1996

INVENTOR(S) : SAVAGE ET AL.

It is certified that error appears in the above-identified patent and that said Letters Patent is hereby corrected as shown below:

Col. 5, line 25: "0f" should read —Of—

Col. 6, line 16: "ears" should read —ear,—

Col. 6, line 21: insert —a— before "proximate"

Col. 6, line 26: "portions" should read —portion—

Col. 6, line 47-48: delete "formed with a first length of smaller cross section and therefore"

Signed and Sealed this

Fifteenth Day of September, 1998

*Attest:*

BRUCE LEHMAN

*Attesting Officer*  *Commissioner of Patents and Trademarks*